United States Patent [19]
Achmatowicz et al.

[11] Patent Number: 4,707,554
[45] Date of Patent: Nov. 17, 1987

[54] METHOD OF OBTAINING DERIVATIVES OF 4β-/1'-ALKEN-1'-YL/-2ξ,5α-DIHYDROXY-3,3aβ-4,5,6,6aβ-HEXAHYDRO-2H-CYCLOPENTA(B)FURAN

[75] Inventors: Barbara Achmatowicz; Andrzej R. Daniewski, both of Burgaska; Stanislaw Marczak, Pulawska; Jacek Pankowski, Goscincowa; Jerzy Wicha, Batorego, all of Poland

[73] Assignee: Polska Akademia Nauk-Instytut Chemii Organicznej, Warsaw, Poland

[21] Appl. No.: 802,702

[22] Filed: Nov. 27, 1985

[30] Foreign Application Priority Data

Dec. 7, 1984 [PL] Poland ................................. 250792
Dec. 7, 1984 [PL] Poland ................................. 250794
Sep. 9, 1985 [PL] Poland ................................. 255296

[51] Int. Cl.$^4$ ........................................ C07D 307/935
[52] U.S. Cl. ................................. 549/214; 549/414; 549/415; 549/465
[58] Field of Search ............... 549/214, 414, 415, 465

[56] References Cited

U.S. PATENT DOCUMENTS 4,094,886  7/1978  Kondo et al. ...................... 549/465
4,420,632  12/1983  Aristoff ............................. 560/119

OTHER PUBLICATIONS

Burks, Jr. et al., J. Org. Chem. 49(24), pp. 4663-4670 (1984).
Attwood et al., J. Chem. Soc. Chem. Comm., pp. 479-481 (1986).
Aristoff et al., J.A.C.S. 107, p. 7967-7974, (1985).
Miller et al., J.A.C.S. 96(21), pp. 6774-6775, (1974).
Field, J.A.C.S. 74, pp. 3919-3921 (1952).
Kocienski, Phosphorous and Sulfur, vol. 24 (1-2), pp. 97-127 (1985).
Morzycki et al., J. U. Chem. 49, pp. 2148-2151 (1984).
Kocienski et al., J. Chem. Soc., Perkin I, pp. 1045-1050 (1980).
Corey et al., J.A.C.S. 91, pp. 5675-5676 (1969).
Kocienski et al., J.C.S. Perkin I, pp. 829-834 (1978).
Julia et al., Tet. Letters, No. 49, pp. 4833-4836, (1973).
Achmatowicz et al., Tetrahedron Letters, 26(45), pp. 5597-6000 (1985).

Primary Examiner—Henry R. Jiles
Assistant Examiner—Bernard I. Dentz
Attorney, Agent, or Firm—Ladas & Parry

[57] ABSTRACT

A new method has been disclosed for obtaining derivatives of 4β-/1'-alken-1'-yl/-2ξ,5=-dihydroxy-3,3aβ,4,5,6,6aβ-hexahydro-2H-cyclopenta [b] furane useful in the synthesis of prostaglandins or their analogs, and a method for obtaining new sulphonyl initial compounds of the general formula 4, in which Z denotes a hydrogen atom or a protective group, Y denotes a group of the formula =CHOZ$^1$, in which Z$^1$ has the meaning stated for Z, whereby protective groups Z and Z$^1$ may be the same or different, and Ar denotes optionally a substituted aryl group.

In the method according to the invention the new sulphonyl derivative of the general formula 4 is alkylated with an electrophilic agent comprising: carbonyl derivatives, oxiranes and halohydrins or their derivatives; the alkylation product is transformed into derivatives of 4β-/1'-alken-1'-yl/-2ξ,5α-dihydroxy-3,3aβ,4,5,6,6aβ-hexahydro-2H-cyclopenta[b] furane in reactions which ensure obtaining a double bond $C_{13}$-$C_{14}$.

New sulphonyl initial compounds of the general formula 4 are obtained from lactone of the general formula 11, in which Z has the above stated meaning and L° denotes a leaving group, which is transformed into a sulphide; the obtained lactone-sulphide is reduced to lactol, and thereafter lactol-sulphide is oxidized to the sulphonyl derivative.

Figure 1:
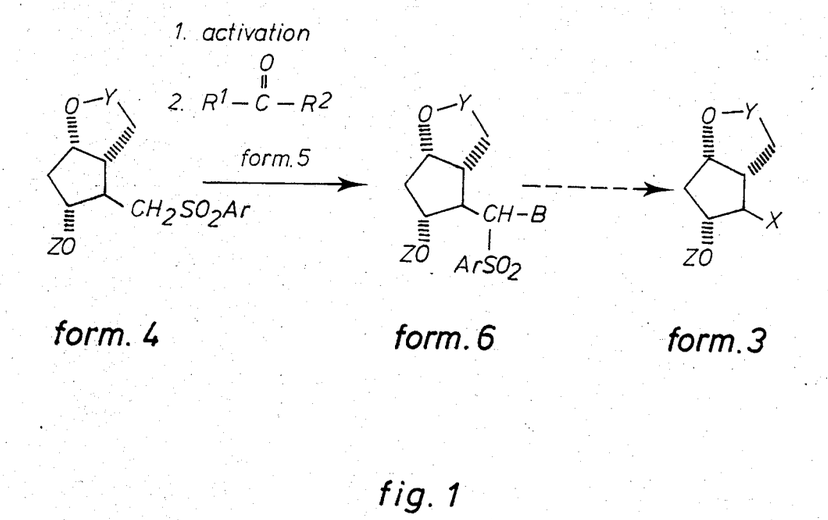
Figure 2:
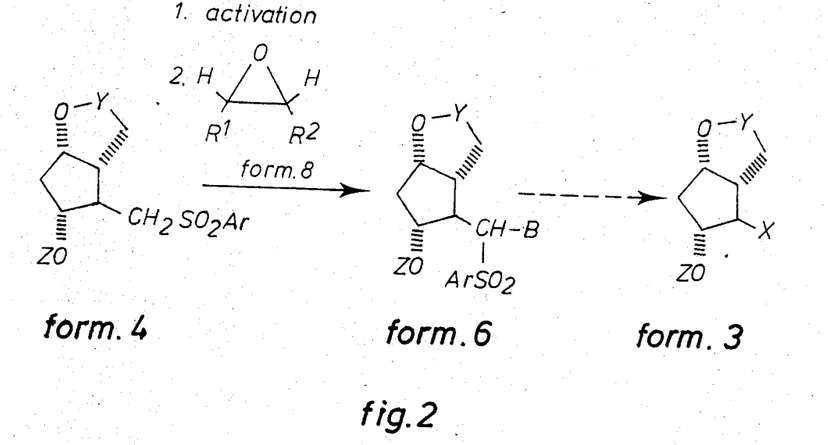
Figure 3:
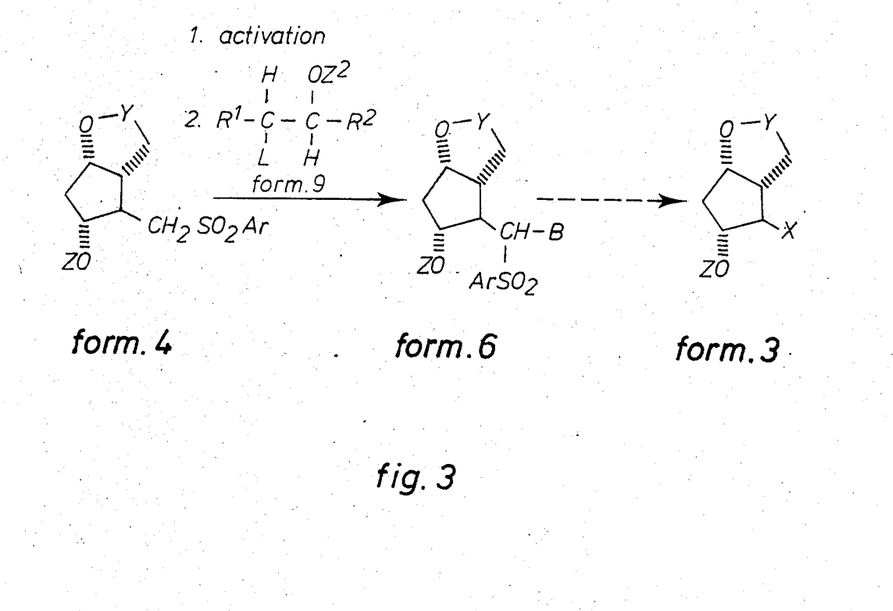
Figure 4:
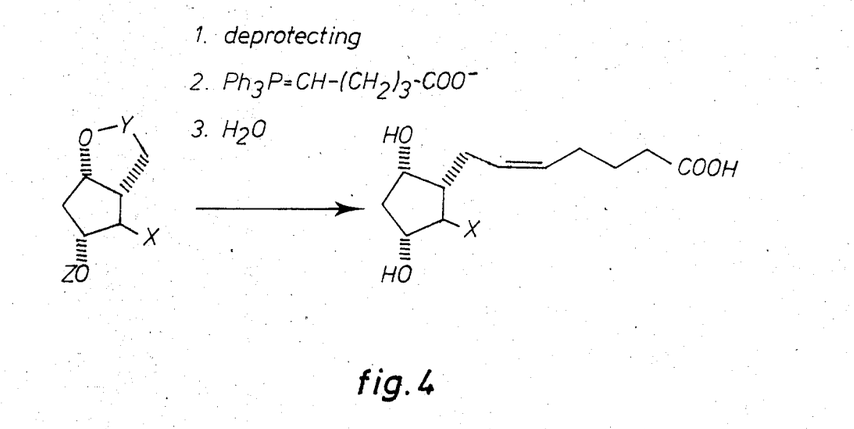
Figure 5:
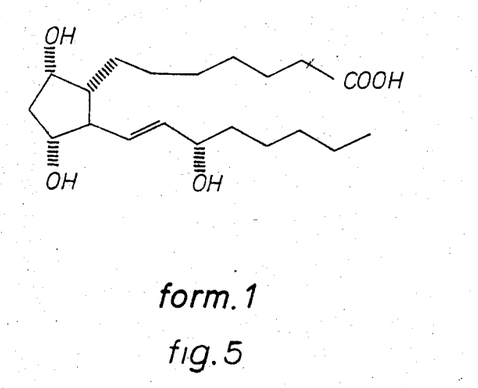
Figure 6:
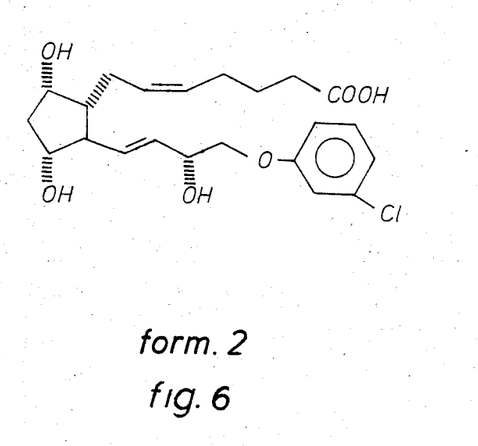
Figure 7:
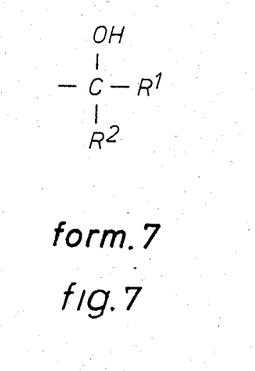
Figure 8:
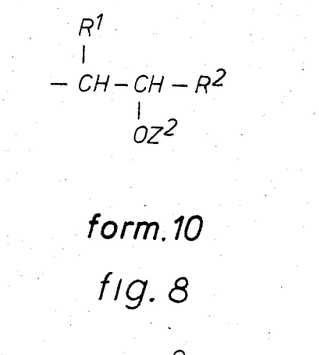
Figure 9:
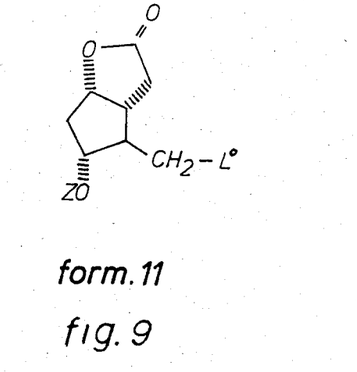
Figure 10:
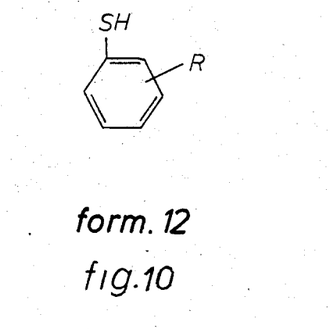
Figure 11:
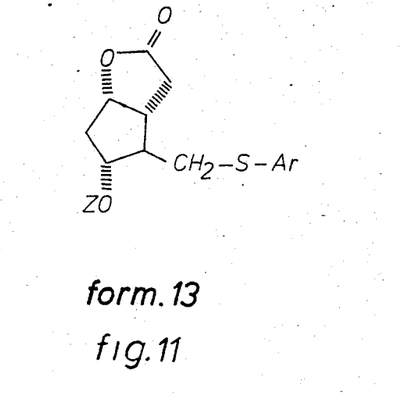
Figure 12:
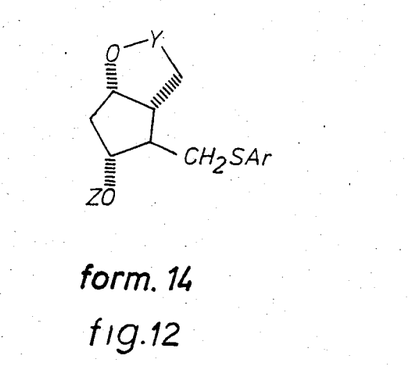
Figure 13:
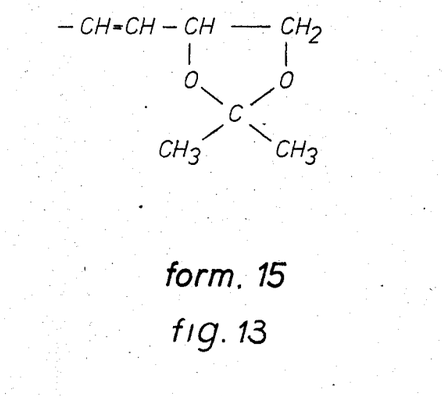
Figure 14:
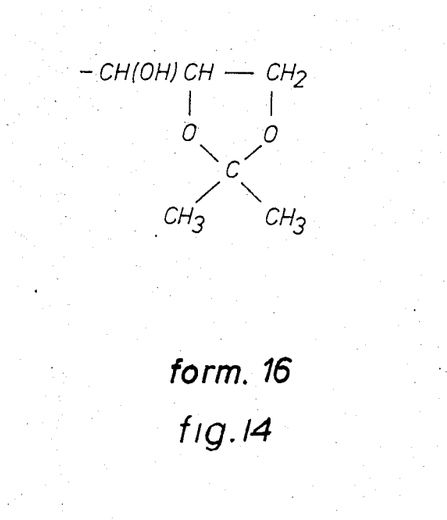

9 Claims, 14 Drawing Figures fig. 1 fig. 2 fig. 3 fig. 4 form. 1 fig. 5 form. 2 fig. 6 form. 7 fig. 7 form. 10 fig. 8 form. 11 fig. 9 form. 12 fig. 10 form. 13 fig. 11 form. 14 fig. 12 form. 15 fig. 13 form. 16 fig. 14

METHOD OF OBTAINING DERIVATIVES OF 4β-/1'-ALKEN-1'-YL/-2ξ,5α-DIHYDROXY-3,3aβ-4,5,6,6aβ-HEXAHYDRO-2H-CYCLOPENTA(B)FURAN

The subject of the present invention is a new method of obtaining derivatives of 4β-/1'-alken-1'-yl/-2ξ,5α-dihydroxy-3,3aβ,4,5,6,6aβ-hexahydro-2H-cyclopenta[b]furane, being the main intermediate products in the process of obtaining prostaglandins and their analogs, among others, prostaglandin $F_{2\alpha}$ and the preparation "Estrumate". The invention relates also to new sulphonyl derivatives of 2H-cyclopenta[b]furane of the general formula 4, in which Ar denotes an aryl group optionally substituted with alkyl, Z denotes a hydrogen atom or a protective group, such as alkyl-, benzyl-, trityl-, tetrahydropyranyl-, alkylsilyl- or acyl group, preferably acetyl-, benzoyl- or p-phenylbenzoyl group, and Y denotes a group of the formula $=CHOZ^1$, in which $Z^1$ has the meaning stated for Z, whereby protective groups Z and $Z^1$ may be the same or different; which are useful as initial compounds in the process of obtaining the above mentioned derivatives of 4β-/1'-alken-1'-yl/-2ξ,5α-dihydroxy-3,3aβ,4,5,6,6aβ-hexahydro-2H-cyclopenta[b]furane.

Prostaglandins are natural compounds having the nature of cellular hormones, regulating numerous biological processes of mammals (F. A. Kuehl, Jr, et al. "Adavances in Prostaglandin and Thromboxane Research", Vol. 1, Eds. B. Samuelsson, R. Paoletti, Raven, N.Y., 1976, p. 313). Both the natural compounds and their synthetic analogs have found an application in medicine and veterinary medicine (P. B. Curtis-Prior, "Prostaglandins: An introduction to their Biochemistry, Physiology and Pharmacology", Elsevier, Amsterdam, 1976). Particularly big practical importance nowadays is that of prostaglandin $F_{2\alpha}$ of the formula 1 and its analog of the formula 2, known under trade names of "Estrumate", "Cloprostanol", "Oestrophan" and others (N. R. A. Beeley et al., Tetrahedron, 31, (Supplement 1), 411 (1981). Besides, prostaglandin $F_{2\alpha}$ is a convenient initial substance for obtaining other prostaglandins, among other things, prostaglandin $E_2$ and $I_2$ (prostacycline), applied also in therapeutics (F. A. Kuehl, Jr, et al. in "Advances in Prostaglandin and Thromboxane Research", Vol. 1, Eds. B. Samuelsson, R. Paoletti, Raven, N.Y., 1976, p. 313).

So far many processes of obtaining prostaglandins and their analogs have been presented and different synthetic intermediate compounds have been proposed [Selected book studies: J. S. Bindra, R. Bindra, "Prostaglandin Synthesis", Academic, N.Y., 1977; A. Mitra, "The Synthesis of Prostaglandin Derivatives", Wiley, N.Y., 1978; G. Szantay, L. Novak "Synthesis of Prostaglandins", Akademiai, Budapest, 1978; R. F. Newton, S. M. Roberts, "Prostaglandins and Thromboxanes", Butterworth Sci., London, 1982].

Derivatives of 4β-/1'-alken-1'-yl/-2ξ,5α-dihydroxy-3,3aβ,4,5,6,6aβ-hexahydro-2H-cyclopenta[b]furane are particularly useful as intermediate compounds in processes conducted on industrial scale because the carbon skeleton of prostaglandin is obtained at one stage, by a stereospecific reaction of these compounds with corresponding Wittig's reagents. At present, widely applied is synthesis of the aforesaid intermediate compounds from Corey's lactone in the process invented by Corey and co-workers, described in J. Am. Chem. Soc., 91, 5675 (1969). The said method enables obtaining racemic as well as optically active prostaglandins by a relatively simple method. It has, however, the following inconveniencies:

- oxidation of "Corey's lactone" to "Corey's aldehyde" must be conducted in exceptionally mild conditions, difficult to attain in technical processes;
- "Corey's aldehyde", as being labile, must be used immediately at the subsequent stage which is the Wittig-Horner's reaction;
- Wittig-Horner's reaction of "Corey's aldehyde" with a corresponding phosphonate yields the required product together with a considerable amount of by-products, mainly the elimination product of the substituent at $C_{11}$ (numeration of prostaglandins) and the neighbouring hydrogen atom and the product of isomerization at $C_{12}$ (Brewster et al., J. Chem. Soc., Perkin I, 1973, 2796; R. Coen et al. Bull. Soc. Chim. Belg., 84, 203, 1975). Thus, this stage of synthesis is inefficient.

Other known methods of obtaining derivatives of 4β-/1'-alken-1¹-yl/-2ξ,5α-dihydroxy-3,3aβ,4,5,6,6aβ-hexahydro-2H-cyclopenta[b]furane (U.S. Pat. specification No. 4,094,886; P. Crabbe et al. J.C.S. Chem. Comm., 1973, 119) are still less appropriate for the reason of a low yield of the stage of obtaining 15-hydroxyl group (numeration of prostaglandins) and the lack of economical methods of obtaining optically active intermediate compounds. Besides, the aforesaid known method is limited only to obtaining the compounds having the hydroxyl geoup in position 15 (numeration of prostaglandins). In order to avoid technical inconveniences and uneconomical stages a new process has been invented. The new process can be conducted on industrial scale.

The subject of the present invention is a method of obtaining derivatives of 4β-/1'-alken-1'-yl/-2ξ,5α-dihydroxy-3,3aβ,4,5,6,6aβ-hexahydro-2H-cyclopenta[b]furane of the general formula 3, in which Z denotes a hydrogen atom or a protective group, Y denotes a group of the formula $=CHOZ^1$, in which $Z^1$ has the meaning stated for Z, whereby protective groups Z and $Z^1$ may be the same or different, and X denotes a straight or a branched alkenyl chain corresponding to a side chain ω of prostaglandins or their analogs, preferably with 2-8 carbon atoms, optionally substituted with such groups as hydroxyl groups, protected hydroxyl groups, oxo groups, protected oxo groups, optionally substituted aryloxyl groups and optionally substituted aryl groups.

The method according to the invention consists in that a new sulphonyl derivative of 2H-cyclopenta[b]furane of the general formula 4, in which Y and Z have the above stated meaning and Ar denotes an optionally substituted aryl group, is alkylated with an electrophilic agent comprising carbonyl derivatives such as aldehydes and ketones, oxiranes and halohydrins or their derivatives; the alkylation product is transformed into derivatives of 4β-/1'-alken-1'-yl/-2ξ,5α-dihydroxy-3,3aβ,4,5,6,6aβ-hexahydro-2H-cyclopenta[b]furane in a reaction or reactions which ensure obtaining a double bond $C_{13}$–$C_{14}$.

The term "protective group" means a derivative of a definite functional group, obtained in order to protect it in conditions of the intended reaction, and next, if necessary, removed with reproduction of the original functional group. To protect hydroxyl functions most often alkyl-, benzyl-, trityl-, tetrahydropyranyl-, alkylsilyland other acyl groups as acetyl-, benzoyl-, p-phenyl-benzoyl- and similar groups are used. To protect carbonyl functions most often acetal arrangements are used, obtained in reactions of the mother carbonyl compound with alcohols like methanol, ethanol and others or with diols like ethylene glycol. In the case when in a molecule of the given compound a hydroxyl- and a carbonyl group are present, and appropriately located, it is possible to protect simultaneously both these groups in the form of intramolecular acetal (derivative of lactol). In the case when in a molecule of the given compound two hydroxyl groups are present in position $\alpha$, $\beta$, it is possible to protect simultaneously both these groups in the form of acetal with a corresponding aldehyde or ketone (obtaining a derivative of methylendioxy, isopropylidendioxy), or to protect each of these groups separately (T. W. Greene, Protective Groups in Organic Synthesis, Wiley, N.Y., 1981).

The term "side chain" refers to aliphatic fragments of a molecule of natural prostaglandins, whereby as chain 60 the fragment $C_1-C_7$ is designated, and as chain $\omega$ the fragment $C_{13}-C_{20}$. This term is applied also to corresponding elements of the structure of analogs of prostaglandins and intermediate products in synthesis of the said compounds. Characteristic examples of alkenyl substituents designated with the symbol X in the formula 3 are groups of the following formulas: $-CH=CH-CH/OZ^2/-nC_5H_{11}$, where $Z^2$ has the meaning stated for Z, whereby protective groups Z and $Z^2$ may be the same or different, and preferably denotes t-butyl-dimethylsilyl group; $-CH=CH-C/O/-n-C_5H_{11}-$; $-CH=CH-CH/OZ/-CH_2-O-C_6H_5$, where Z has the above stated meaning, and the phenyl ring can be substituted, preferably with a chlorine atom in the meta-position; $-CH=CH-C_6H_5$; $-CH=C/CH_3/_2$; $-CH=CH-n-C_6H_{13}$; $-CH=CH-Het$, in which Het denotes a heterocyclic substituent, obtained by simultaneous protection of two hydroxyl groups in the position $\alpha$, $\beta$, such as dioxolan and similar ones; $-CH=CR^1R^2$, where $R^1$ denotes an aliphatic substituent, e.g. methyl, and $R^2$ denotes an aliphatic substituent, e.g. n-hexyl. In the process according to the invention the new sulphonyl derivative of the general formula 4, in which Y and Z have the above stated meaning and Ar denotes an optionally substituted aryl group, is first of all reacted with an organometallic compound of the type of a strong base capable of producing carbanion in the position neighbouring with the sulphonyl group and, optionally, with salt of metal. Typical strong bases comprise organometallic compounds like lithium amides, e.g. lithium diisopropylamide, lithium hexamethyldisilasate, lithoalkanes, preferably n-butyllithium, Grignard's compounds, as for example, magnesium methylbromide. As a salt of metal it is possible to use compounds having the properties of Lewis's acids. Such salts include magnesium-, zinc-, titanium- and boron halides, preferably magnesium chloride, zinc chloride, titanium tetrachloride or boron trifluoride. The reaction should be preferably conducted in aprotic solvents such as, for example, lower ethers, tetrahydrofurane, dimethoxyethane, in a low temperature, in inert atmosphere. The sulphonyl derivative thus activated is treated with an electrophilic agent being a carbonyl derivative of the general formula 5, in which one of $R^1$ and $R^2$ denotes a hydrogen atom and the other one denotes a straight or branched alkyl group, preferably with 2-7 carbon atoms, optionally containing such substituents like hydroxyl groups, protected hydroxyl groups, oxo groups, protected oxo groups, optionally substituted aryloxyl groups and optionally substituted aryl groups, or the other one of $R^1$ and $R^2$ denotes optionally substituted aryl group, preferably a phenyl group or a substituted phenyl group, like tolyl group; or in which $R^1$ and $R^2$ denote the same or different alkyl or aryl groups. The intermediate compound thus obtained, of the general formula 6, in which Y and Z have the above stated meaning and B denotes a group of the formula 7 in which Ar, $R^1$ and $R^2$ have the above stated meaning, are reduced, in the result of what the $ArSO_2$ group together with the neighbouring hydroxyl group is removed and an alkenyl side chain is formed, which has the formula $-CH=CR^1R^2$, in which $R^1$ and $R^2$ have the above stated meaning. The reducing agent may be, for example, zinc, sodium amalgam, tri-n-butyl-tin hydride and the like. The reaction should be preferably conducted with the use of sodium amalgam in lower alcohols like methanol, in ambient temperature, in neutral atmosphere. Other reducing agents like, for example, zinc in lower alcohols, yield also satisfactory results. The alternative method of removing the arylsulphonyl group together with the neighbouring hydroxyl group includes the following operations: the intermediate compound of the general formula 6 is first of all esterificated by means of acylating agents and thereafter the acyl derivative thus obtained is reduced. Acylating agents may be acid anhydrides, aroyl-, alkanoyl-, alkyl- or arylsulphonyl halides, preferably benzoyl cloride, acetyl chloride, mesyl chloride and the like. Reduction can be, for example, conducted with the use of sodium amalgam or similar reducing agents as the above described ones. From the product thus obtained, if necessary, protective groups are removed. In the equivalent modification of the method according to the invention the activated sulphonyl derivative of the general formula 4, in which Ar, Y and Z have the above stated meaning, is reacted with an electrophilic agent selected from among oxiranes of the general formula 8 or derivatives of the general formula 9; where one of $R^1$ and $R^2$ denotes a hydrogen atom and the other one denotes an alkyl group having a straigh or branched chain optionally comprising such substituents like aryloxyl groups, substituted aryloxyl groups, aryl groups, substituted aryl groups, or the other one of $R^1$ and $R^2$ denotes optionally substituted aryl group, preferably a phenyl or tolyl group; or in which $R^1$ and $R^2$ denote the same or different alkyl- or aryl groups; L denotes a leaving group; and $Z^2$ has the meaning stated for Z, whereby protective groups Z and $Z^2$ may be the same or different.

The reaction is preferably conducted in aprotic solvents such as, for example, lower ethers, tetrahydrofurane, dimethoxyethane, in a low temperature, in inert atmosphere. In the case of applying the electrophilic agent of the general formula 9 the preferable temperature range is from $-78°$ C. up to $20°$ C. In the aforesaid reaction of alkylation an intermediate compound of the general formula 6 is obtained, in which Y and Z have the above stated meaning, and B denotes a group of the formula 10 in which Ar, $R^1$, $R^2$ and $Z^2$ have the above stated meaning, on condition that in the case of using an electrophilic agent of the formula 8 the substituent $Z^2$ denotes only a hydrogen atom. In the compound thus obtained, if necessary, the protection of hydroxyl groups is partially released and thereafter the said compound is oxidized and, optionally, treated with a base, in the case of using an agent of the formula 8, a base or an acid. This operation leads to removal of the Ar—SO$_2$ group and the neighbouring hydrogen atom and, in consequence, to formation of an alkenyl side chain ω. From the product thus obtained, if necessary, protective groups are removed. In order to obtain derivatives of the formula 3, in which X denotes a side chain ω devoid of the ketone group, the derivative thus obtained is reduced by conventional methods. The above tranasformations are illustrated by diagrams 1, 2 and 3. In general, oxidizing agents may be chromium salts, dimethylsulphoxide in combination with activating agents such as oxalyl chloride, dicyclohexylcarbodiimide and the like, preferably pyridiniumchlorchromate. As the base it is possible to use tertiaty amines, preferably triethylamine or diazabicycloundecane. In the case when as the electrophilic agent a compound of the formula 8 is used, the oxidation reaction is preferably conducted by means of mild oxidizing agents such as dimethylsulphoxide and oxalyl chloride, dimethylsolphoxide and dicyclohexylcarbodiimide, thioanisole-chlorine in the presence of a base such as triethylamine, or reactants based on chromium (VI), such as pyridiniumchlorchromate, chromium trioxide-pyridine, and the like. As the base it is possible to use preferably amines, such as triethylamine, diazabicycloundecane (DBU), tetramethylguanidine. The acid may be silica gel, acid resins, for example, Amberlyst XN-1010 and the like.

The term "leaving group" means an atom or a group susceptible to nucleophilic substitution. Typical leaving groups include a halogen atom, like a iodine- or bromine atom, an arylsulphonoxyl- and alkylsulphonoxyl group, preferably a tosyloxyl-, mesyloxyl group and the like. Aryl or aryloxyl substituents may be such groups as, for example, optionally substituted phenyl group or optionally substituted phenoxyl group. An aryl substituent with the symbol Ar may be, for example, a phenyl- or tolyl group. Initial sulphonyl derivatives of the general formula 4, in which Ar, Y and Z have the above stated meaning, are new compounds. A preferable method of obtaining thereof consists in that a compound of the general formula 11, in which Z has the above stated meaning, and L denotes a leaving group, is reacted with thiophenol of the general formula 12, in which R denotes a hydrogen atom or an alkyl substituent, in the presence of a base. The base means a compound capable of yielding a thiophenolate anion. Typical bases include metal alcoholates like, for example, potassium t-butoxylate, metal hydrides like, for example, sodium hydride, lithioalkanes like, for example, n-butyllithium and the like. The reaction can be conducted in polar solvents neutral in relation to reactants, such as dimethylsulphoxide, dimethylformamide and the like, in a room temperature, without any special heating or cooling. Thus obtained sulphide of the general formula 13, in which Ar and Z have the above stated meaning are reduced and, optionally, hydroxyl groups are protected, whereby the obtained compound of the general formula 14, in which Y, Ar and Z have the above stated meaning, is oxidized to a sulphonyl derivative. From the product thus obtained, if necessary, protective groups are removed by the known methods. As the reducing agent it is possible to use metal hydrides, preferably diisobutylaluminium hydride. Preferable agents oxidizing the sulphide group to the sulphonic group include, for example, m-chloroperbenzoic acid and sodium periodate. Examples of "leaving groups" of the symbol L° in the formula 11 may be the previously mentioned groups or atoms. Initial diols of the general formula 11 can be obtained from lactones described and obtained by the method presented in the work: J. Tomoskozi, L. Gruber, G. Kovacs, J. Szekely, V. Simonidesz, Tetrahedron Letters 1976, 4639.

Derivatives of 4β-/1'-alken-1'-yl/-2ξ,5α-dihydroxy-3,3aβ,4,5,6,6aβ-hexahydro-2H-cyclopenta[b]furane obtained by the method according to the invention are transformed into corresponding prostaglandins or their analogs by building an additional fragment of the chain α comprising atoms of carbon $C_1$–$C_5$, according to the method described by E. J. Corey and R. Noyori, Tetrahedron Letters, 1970, 311, as illustrated by diagram 4.

The below presented examples illustrate the invention without limiting its scope.

EXAMPLE I

Obtaining of 4β-/benzensulphonylmethyl/-5α-/t-butyldimethylsilyloxy/-2ξ-methoxy-3,3aβ,4,5,6,6aβ-hexahydro-2H-cyclopenta[b]furane {formula 4, Ar=C$_6$H$_5$, Y=CHOCH$_3$, Z=Si/t—C$_4$H$_9$/CH$_3$/$_2$}.

A. Obtaining of racemic 4β-/thiophenoxymethyl/-5α-hydroxy-3,3aβ,4,5,6,6aβ-hexahydro-2H-cyclopenta[b]furan-2-one (formula 13, Ar=C$_6$H$_5$, Z=H).

To a solution of thiophenol /formula 12, R=H/ 0.8 g, 7.5 mmole/ in dimethylsulphoxide /6 ml/, mixed in the atmosphere of argon, potassium t-butoxylate /0.9 g, 7.5 mmole/ was added and then a solution of 4β-/p-toluen-sulphoxymethyl/-5α-hydroxy-3,3aβ,4,5,6,6aβ-hexahydro-2H-cyclopenta[b]furan-2-one {formula 11, L°=OSO$_2$—C$_6$H$_4$—pCH$_3$, Z=H /2 g, 6.2 mmole/ in dimethylsulphoxide /6 ml/. The reaction mixture was maintained for 30 minutes in a room temperature, and thereafter it was diluted with chloroform /60 ml/, washed with water, dried, and the solvent was evaporated under reduced pressure. The residue was applied on a column with silica gel /25 g/ and the column was washed with a mixture of hexane, chloroform and ethyl acetate at the ratio of 1:1:1. The title sulphide /1.58 g, 98%/ in the form of a crystalline substance was obtained. An analytic sample was recrystallized from a mixture of ether and hexane, melting point 62°–63° C., infrared spectrum, γ$_{max}$ /CHCl$_3$/ 3420 /OH/, 1750 /C=O/, 1200 /C—O—C/ cm$^{-1}$; spectrum $^1$H NMRδ /ppm/ 7.4 /m, 5H/, 5.05 /m, 1H/, 4.2 /m, 1H/, 3.3–1.9 /m, 8H/.

Elementary analysis
Calculated for C$_{14}$H$_{16}$O$_3$S /264.3/: %C—63.61; %H—6.10; %S—12.13. Found: %C—63.52; %H—5.95; %S—12.40.

B. Obtaining of 4β-/thiophenoxymethyl/-2ξ,5α-dihydroxy-3,3aβ,4,5,6,6aβ-hexahydro-2H-cyclopenta[b]furane {formula 14, Ar=C$_6$H$_5$, Y=CHOH, Z=H}.

To the solution of the compound obtained at stage A /528 mg, 2 mmoles/ in methylene chloride /10 ml/, mixed in the atmosphere of argon, at a temperature of −78° C., a 1.2M solution of diisobutylaluminium hydride in toluene /6.5 ml, 8 mmoles/ was added dropwise. Stirring at a temperature of −78° C. was being carried on for 30 minutes, and then methanol /5 ml/ was added dropwise, silica gel /3 g/ was added and the mixture thus obtained was evaporated under reduced pressure. The dry residue was transferred to a column with silica gel /45 g/ and the column was eluted with a mixture of chloroform, ethyl acetate and methanol at the ratio of 100:100:2. The title lactol /400 mg, 75%/ in the form of colourless syrup was obtained; γ$_{max}$ /CHCl$_3$/ 3360 /OH/ cm$^{-1}$. The analytic sample was again subject to chromatography and was dried in high vacuum.

Elementary analysis

Calculated for $C_{14}H_{18}O_3S$ /266.3/: %C—63.13; %H—6.81; %S—12.04. Found: %C—62.95; %H—6.67; %S—12.21.

C. Obtaining of 4β-/thiophenoxymethyl/-5α-hydroxy-2ξ-methoxy-3,3aβ,4,5,6,6aβ-hexahydro-2H-cyclopenta[b]furane {formula 14, Ar=$C_6H_5$, Y=-CHOCH$_3$, Z=H}.

To a solution of lactol obtained at stage B /536 mg, 2 mmole/ in methanol /16 ml/, mixed at a temperature of −20° C., boron trifluoride etherate /0.2 ml/ was added. After 2 hours a few drops of triethylamine were added, the mixture was brought to the room temperature and the solvent was evaporated under reduced pressure. The residue was dissolved in chloroform and filtered through silica gel /2 g/. After evaporation of chloroform the title acetal /570 mg, 95%/ was obtained in the form of thick syrup; $\gamma_{max}$ /CHCl$_3$/ 3370 /OH/ cm$^{-1}$. The analytic sample was again subject to chromatography and was dried in high vacuum.

Elementary analysis

Calculated for $C_{15}H_{20}O_3S$ /280.4/: %C—64.25; %H—7.19; %S—11.44. Found: %C—64.39; %H—7.10; %S—11.55.

D. Obtaining of 4β-/thiophenoxymethyl/-5α-/t-butyldimethylsyliloxy/-2ξ-methoxy-3,3aβ,4,5,6,6aβ-hexahydro-2H-cyclopenta[b]furane {formula 14, Ar=$C_6H_5$, Y=CHOCH$_3$, Z=Si/t—$C_4H_9$//CH$_3$/$_2$}.

To a solution of the compound obtained at stage C /570 mg, 2 mmoles/ in dimethylformamide /1.6 ml/, mixed in the atmosphere of argon, in a room temperature, imidazole /340 mg, 5 mmoles/ and t-butyldimethylsilyl chloride /370 mg, 3 mmoles/ were subsequently added. The mixture thus obtained was maintained at a temperature of 40° C. for 10 minutes, then it was cooled, diluted with methylene chloride /20 ml/, washed with water, 3% hydrochloric acid saturated solution of sodium bicarbonate, and dried /Na$_2$SO$_4$/. After evaporation of the solvent the title crude compound /785 mg/ was obtained, which was purified by filtration through silica gel /5 g/ with the use of chloroform as the eluent. The title compound /710 mg, 88%/ in the form of thick syrup was obtained; $\gamma_{max}$ no characteristic absorption; spectrum $^1$H NMR δ /ppm/ 7.3 /m, 5H, aromatic protons/, 5.1 /m, 1H, C$_2$H—/, 4.5 /m, 1H, C$_{6a}$—H/, 4.0 /m, 1H, C$_5$—H/, 3.3 /2s, 3H, OCH$_3$/, 0.9 /s, 9H, CH$_3$—C—Si/. The analytic sample was dried in high vacuum.

Elementary analysis

Calculated for $C_{21}H_{34}OSSi$ /394.6/: %C—63.91; %H—8.68; %S—8.12. Found: %C—63.80; %H—8.80; %S—8.31.

E. To a solution of the compound described at stage D /1.1 g, 2.7 mmoles/ in methylene chloride /50 ml/, mixed in the atmosphere of argon, at a temperature of −78° C., a solution of m-chlorperbenzoic acid /80%/, 1.4 g, 6.5 mmole/ in methylene chloride /30 ml/ was dropped in. The mixture was maintained at a temperature of 0° C. for 2 hours, and then was diluted with chloroform and washed subsequently with saturated solution of sodium thiosulphate, saturated solution of sodium bicarbonate and brine. After drying, the solvent was evaporated under reduced pressure, yielding title sulphone in the form of crystalline substance; $\gamma_{max}$ /CHCl$_3$/ 1315, 1150 and 840 cm$^{-1}$; $^1$H NMR 8.05 and 7.75 /m, 5H, aromatic protons/, 5.13 /m, 1H, C$_2$—H/, 4.55 /m, 1H, C$_{6a}$—H/, 3.87 /m, 1H, C$_5$—H/, 3.34 /2s, 3H, —OCH$_3$/, 0.9 /s, 9H, Si—C—CH$_3$/. Crystallization of the crude product /ether-hexane/ yielded an analytic sample of the melting point of 69°-70° C.

Elementary analysis

Calculated for $C_{21}H_{34}O_5SSi$ /426.6/: %C—59.12; %H—8.03; %S—7.52. Found: %C—59.24; %H—7.85; %S—7.80.

EXAMPLE II

Obtaining of 4β-[3'ξ-/t-butyldimethoxysilyloxy/-1'-octene-1'-yl]-5α-/t-butyldimethylsilyloxy/-2ξ-methoxy-3,3aβ,4,5,6,6aβ-hexahydro-2H-cyclopenta[b]furane {formula 3, X=—CH=CH—CH[OSi/t—$C_4H_9$//CH$_3$/$_2$]—n$C_5H_{11}$, Y=CH—OCH$_3$, Z=Si/t—$C_4H_9$//CH$_3$/$_2$}.

To a solution rac 4β-/benzensulphonylmethyl/-5α-/t-butyldimethylsilyloxy/-2ξ-methoxy-3,3aβ,4,5,6,62β-hexahydro-2H-cyclopenta[b]furane [formula 4, Ar=—$C_6H_5$, Y=CH—OCH$_3$, Z=Si/t—$C_4H_9$//CH$_3$/$_2$] /427 mg, 1 mmole/ in tetrahydrofurane /5 ml/, mixed in the atmosphere of argon at the temperature of −70° C., n-butyllithium /1.4M in hexane, 0.7 ml, 1 mmole/ was added. After three minutes etherate of boron trifluoride /0.12 ml, 1 mmole/ was added, and after further 10 minutes 2-/t-butyldimethylsilyloxy/-heptanal {formula 5, R$^1$=H, R$^2$=CH—[OSi/t—$C_4H_9$/CH$_3$/$_2$]—n$C_5H_{11}$} /260 mg, 1 mmole/ was added. The temperature of the reaction mixture was raised to −18° C. during about 1.5 hours and the said temperature was being maintained for further 16 hours. After that time a solution of ammonium chloride in tetrahydrofurane was added, the mixture was extracted with methylene chloride (3×10 ml) and the combined extracts were washed with brine, dried /MgSO$_4$/ and the solvent was evaporated. The obtained product was 4β-[1'ξ-/benzensulphonyl/-2'ξ-hydroxy-3'ξ-/t-butyldimethylsilyloxy/-1'-octyl]-5α-/t-butyldimethylsilyloxy/-2ξ-methoxy-3,3aβ,4,5,6,6aβ-hexahydro-2H-cyclopenta[b]furane {formula 6, Ar=$C_6H_5$, B=—CH/OH/—CH[OSi/t—$C_4H_9$//CH$_3$/$_2$]—n$C_5H_{11}$, Y=CHOCH$_3$, Z=Si/t—$C_4H_9$//CH$_3$/$_2$} /990 mg/, which was dissolved in methanol /8 ml/ and was treated in the atmosphere of argon with 6% sodium amalgam /5 g/ during 2 hours. The clear solution was decanted from above the remaining amalgam, diluted with water of the temperature of 0°-5° C. and extracted with benzene. The organic extract was washed with brine and dried /Na$_2$SO$_4$/, and thereafter the solvent was evaporated under reduced pressure. The crude title compound /600 mg, 80%/ was obtained in the form of thick syrup; spectrum $^1$H NMR δ /ppm/ 5.5 /m, 2H, vinyl protons/; 5.1 /m, 1H, C$_2$—H/, 4.9-3.4 /m, 4H/ 3.25 /width s, 3H, OCH$_3$/, 0.9 /s, 18H, Si—C—CH$_3$/, 0.85 /width t, 3H, CH$_2$CH$_3$/. The analytic sample was distilled at the temperature of 180° C. /0.2 mm Hg/.

Elementary analysis

Calculated for $C_{28}H_{56}O_4Si_2$/512.9/: %C—65.56; %H—11.01. Found: %C—65.72; %H—11.29.

EXAMPLE III

Obtaining of 4β-/1'-octene-1'-yl/-5α-/t-butyldimethylsilyloxy/-2ξ-methoxy-3,3aβ,4,5,6,6aβ-hexahydro-2H-cyclopenta[b]furane [formula 3, X=—CH=CH—n—$C_6H_{13}$, Y—CHOCH$_3$, Z=Si/t—$C_4H_9$//CH$_3$/$_2$].

Operations as in example II until the moment of adding etherate of boron fluoride, and then, after 10 minutes, heptanal /formula 5, $R^1=H$, $R^2=n-C_6H_{13}$/ /130 mg, 1.1 mmole/ was dropped in. Temperature of the reaction mixture was raised up to $-20°$ C. during 1.5 hours and the said temperature was maintained for further 16 hours. After that time a solution of ammonium chloride in tetrahydrofurane was added and the mixture thus obtained was extracted with methylene chloride /3×10 ml/. The combined extracts were washed with brine, dried /MgSO$_4$/ and the solvent was evaporated under reduced pressure. The obtained product was crude 4β-[1'ξ-/benzensulphonyl/-2'ξ-hydroxy-1'-octyl]-5α-/t-butyldimethylsilyloxy/-2ξ-methoxy-3,3aβ,4,5,6,6aβ-hexahydro-2H-cyclopenta[b]furane [formula 6, Ar=C$_6$H$_5$, B=—CH/OH/—nC$_6$H$_{13}$, Y=-CHOCH$_3$, Z=Si/t—C$_4$H$_9$//CH$_3$/2] /700 mg/, which was dissolved in methanol /5 ml/ and treated in the atmosphere of argon with 6% sodium amalgam /3 g/ during 2 hours. The clear solution was decanted from above the remaining amalgam, diluted with cold water and extracted with benzene. The organic extract was washed with brine and dried /MgSO$_4$/, and thereafter the solvent was evaporated under reduced pressure. The crude title compound /480 mg, 96%/ was obtained in the form of thick syrup; spectrum $^1$H NMR δ /ppm/ 5.5 /m, 2H, vinyl protons/, 5.2 /m, 1H, C$_2$—H, 3.25 /width s, 3H, OCH$_3$/, 0.9 /s, 9H, Si—C—CH$_3$/. The analytic sample was distilled at the temperature of 160° C. /1 mm Hg/.

Elementary analysis

Calculated for C$_{22}$H$_{42}$O$_3$Si /334.6/: %C—78.95; %H—12.65. Found: %C—78.80; %H—12.82.

EXAMPLE IV

Obtaining of 4β-/2'-phenylethene-1'-yl/-5α-/t-butyldimethylsilyloxy/-2ξ-methoxy-3,3aβ,4,5,6,6aβ-hexahydro-2H-cyclopenta[b]furane [formula 3, X=—CH=CH—C$_6$H$_5$, Y=CHOCH$_3$, Z=Si/t—C$_4$H$_9$//CH$_3$/2].

Operations as in example II until the moment of adding etherate of boron trifluoride, and then after 10 minutes benzoic aldehyde /formula 5, $R^1$=H, $R^2$=C$_6$H$_5$/ /110 mg, 1.1 mmole/ was dropped in. Temperature of the reaction mixture was raised up to $-20°$ C. during 1 hour and the said temperature was maintained for further 8 hours. After that time a solution of ammonium chloride in tetrahydrofurane was added and the mixture thus obtained was extracted with methylene chloride. The combined extracts were washed with brine, dried /MgSO$_4$/ and the solvent was evaporated under reduced pressure. The obtained product was crude 4β-[1'-/benzensulphonyl/-2'ξ-hydroxy-2'-phenyl-1'-ethyl]-5α-/t-butyldimethylsilyloxy/-2ξ-methoxy-3,3aβ,4,5,6,6aβ-hexahydro-2H-cyclopenta[b]furane [formula 6, Ar=C$_6$H$_5$, B=—CH/OH/C$_6$H$_5$, Y=CHOCH$_3$, Z=Si/t—C$_4$H$_9$//CH$_3$/2] /500 mg/, which was dissolved in methanol /5 ml/ and treated in the atmosphere of argon with 6% sodium amalgam /3 g/ during 3 hours. The clear solution was decanted from above the remaining amalgam, diluted with cold water and extracted with benzene. The organic extract was washed with brine and dried /MgSO$_4$/, and thereafter the solvent was evaporated under reduced pressure. The title compound in the form of thick syrup was obtained. The analytic sample was subject to chromatography and was dried in high vacuum.

Elementary analysis

Calculated for C$_{24}$H$_{34}$O$_3$Si /374.6/: %C—70.54; %H—9.15. Found: %C—70.30; %H—9.20.

EXAMPLE V

Obtaining of 4β-/2'-phenylethene-1'-yl/-5α-t-butyldimethylsilyloxy/-2ξ-methoxy-3,3aβ,4,5,6,6aβ-hexahydro-2H-cyclopenta[b]furane.

To the solution of rac 4β-/benzensulphonylmethyl/-5α-/t-butyldimethylsilyloxy/-2ξ-methoxy-3,3aβ,4,5,6,6aβ-hexahydro-2H-cyclopenta b furane /formula 4, Ar=C$_6$H$_5$, Y=CH—OCH$_3$, Z=Si/t-C$_4$H$_9$//CH$_3$/2 /427 mg, 1 mmole/ in tetrahydrofurane /25 ml/, mixed in the temperature of $-78°$ C., in the atmosphere of argon, n-butyllithium /1.4M in hexane, 0.8 ml, 1.1 mmole/ was added, and then benzoic aldehyde /120 mg, 1.1 mmole/ was dropped in. The reaction mixture was maintained at the temperature of $-60°$ C. for 3 hours and was kept at a room temperature for 16 hours. After that time a saturated solution of ammonium chloride /0.5 ml/ was added, the mixture thus obtained was extracted with methylene chloride /3×10 ml/, the combined extracts were washed with brine and dried /MgSO$_4$/. After evaporation of the solvent under reduced pressure crude 4β-[1'-/benzensulphobyl/-2'ξ-hydroxy-2'-phenyl-1'-ethyl]-5α-/t-butyldimethylsilyloxy/-2ξ-methoxy-3,3a//β,4,5,6,6aβ-hexahydro-2H-cyclopenta[b]furane /formula 6, Ar=C$_6$H$_5$, B=—CH/OH/C$_6$H$_5$, Y=CHOCH$_3$, Z=Si/t-C$_4$H$_9$//CH$_3$/2/ was obtained, which was purified by chromatography on silica gel with the use of a mixture of hezane and ethyl acetate at the ratio of 3:1 for elution. The purified product thus obtained /399 mg, 75%/ showed in the infrared spectrum the maximum absorption at 3500 cm$^{-1}$ /film/ and in the spectrum $^1$H NMR the following signals: δ /CDCl$_3$/ ppm 0.85 /s, 9H/, 1.0-2.7 /m, 9H/, 3.21 /s, 3H/, 3.95-4.25 /m, 1H/, 5.0-5.2 /m, 1H/, 7.1-8.2 /m, 10H/. The aforesaid product was dissolved in methanol /5 ml/ and treated in the atmosphere of argon with 6% sodium amalgam /3 g/ during 3 hours. The clear solution was decanted from above the remaining amalgam, diluted with cold water and extracted with benzene. The organic extract was washed with brine and dried /MgSO$_4$/, and thereafter the solvent was evaporated under reduced pressure. The title compound thus obtained /150 mg/ was identical with the one described in example IV.

EXAMPLE VI

Obtaining of 4β-/3'-oxo-1'-octene-1'-yl/-5α-/-t-butyldimethylsilyloxy/-2ξ-methoxy-3,3aβ,4,5,6,6aβ-hexahydro-2H-cyclopenta[b]furane. To a solution of 4β-/benzensulphonylmethyl/-5α-/t-butyldimethylsilyloxy/-2ξ-methoxy-3,3aβ, 4,5,6,6aβ-hexahydro-2H-cyclopenta[b]furane /formula 4, Ar=—C$_6$H$_5$, Y=-CHOCH$_3$, Z=Si/t-C$_4$H$_9$/ /CH$_3$/2/ /427 mg, 1 mmole/ in tetrahydrofurane /4 ml/, mixed in the atmosphere of argon at the temperature of $-72°$ C., n-butyllithium /1.4M in hexane, 0.76 ml, 1.1 mmole/ was added. The mixture was maintained at the temperature of $-72°$ C. for 30 minutes, and then boron trifluoride etherate /0.125 ml, 1 mmole/ was added, and, subsequently, 1,2-epoxyheptane /formula 8, $R^1$=H, $R^2$=—nC$_5$H$_{11}$/ /130 mg, 1 mmole/. Stirring at the temperature of $-72°$ C. was being carried on for 1.5 hours, and thereafter the temperature was raised up to 0° C. during about 1 hour and a saturated aqueous solution of ammonium chloride /0.5 ml/ was added. The mixture was extracted with methylene chloride /2×5 ml/, the combined extracts were washed with brine and dried /MgSO$_4$/. The solvent was evaporated, and the residue /550 mg/ was applied on a column with silica gel /MN 100–200, 11 g/. Elution of the column with a mixture of toluene with ethyl acetate at the ratio of 10:1 yielded 4β-[1'ξ-/benzensulphonyl/-3'ξ-hydroxy-1'-octyl]-5α-/t-butyldimethylsilyloxy/-2ξ-methoxy-3,3aβ, 4,5,6,6aβ-hexahydro-2H-cyclopenta[b]furane [formula 6, Ar=$C_6H_5$, B=$CH_2CH/OH/-nC_5H_{11}$, Y=$CHOCH_3$, Z=Si/t-$C_4H_9//CH_3/_2$] /485 mg, 90%/; $\gamma_{max}$ /film/ 3600–3200 /OH/, 1470 and 1450 /$SO_2C_6H_5$/, 1255 /C—O—C/, 840 cm$^{-1}$; $^1$H NMR /CDCl$_3$/ δ /ppm/ 0.03 /s, 6H, SiCH$_3$/, 0.8–0.9 /singlet overlapping multiplet, 12H, SiCCH$_3$ and CH$_2$CH$_3$/, 2.2–2.8 /m, 16H/, 3.34 /s, 3H, OCH$_3$/, 3.5–4.0 /m, 2H, C$_5$H and C$_3$H/, 4.6 /m, 1H, C$_{6a}$H/, 5.10 /m, 1H, C$_2$H/, 7.5–7.75 /m, 3H, aromatic H/;

Elementary analysis
Calculated for $C_{28}H_{48}O_6SSi$: %C—62.18; %H—8.95. Found: /541.41/ %C—62.33; %H—9.03.

The above described compound /450 mg, 0.83 mmole/ was dissolved in methylene chloride /1 ml/ and was added dropwise at the temperature of −50° C., in the atmosphere of argon, at intensive stirring into an oxidizing mixture prepared, as follows: to a mixture of oxalyl chloride /0.08 ml, 0.97 mmole/ and methylene chloride /2 ml/, cooled at stirring in the atmosphere of argon to −60° C., a mixture of dimethylsulphoxide /0.14 ml, 1.97 mmole/ and methylene chloride /0.4 ml/ was added, with maintenance of the temperature below −50° C. The reaction mixture was maintained for 30 minutes at the temperature of −50° C., then triethylamine /0.6 ml/ was dropped in, and after further 5 minutes the cooling bath was removed. When the reaction mixture reached the room temperature /about 1 hour/ water /5 ml/ was added, layers were separated and the water layer was extracted with methylene chloride /2×5 ml/. The combined organic solutions were washed with brine, dried /MgSO$_4$/ and the solvent was evaporated. The residue /480 mg/ was applied on a column with silica gel /MN 100–200, 10 g/ and the column was eluted with a mixture of toluene and ethyl acetate, 9:1. The obtained product was 4β-[1'-/benzensulphonyl/-3'-oxo-1'-octyl]-5α-/t-butyldimethylsilyloxy/-2ξ-methoxy-3,3aβ,4,5,6,6aβ-hexahydro-2H-cyclopenta[b]furane /formula 6, Ar=$C_6H_5$, B=$CH_2C/O/-nC_5H_{11}$, Y=$CHOCH_3$, Z=Si/t-$C_4H_9$/ /CH$_3$/$_2$ /400 mg, 89%/; $\gamma_{max}$ /film/ 1720 /C=O/, 1470 and 1450 /aromat/, 1310 /SO$_2$Ph/, 1255 and 840 cm$^{-1}$; high resolution mass spectrum for $C_{24}H_{37}O_6SSi$ /M$^+$—C$_4$H$_9$/ calculated: 481,2087. found: 481,2107

To a solution of the above described compound /378 mg, 0.7 mmole/ in tetrahydrofurane /20 ml/, mixed at a room temperature in the atmosphere of argon, a solution of diazabicycloundecane /105 mg, 0.7 mmole/ was added dropwise. Stirring at a room temperature was being carried on for 4 hours, and thereafter the reaction mixture was diluted with chloroform /20 ml/, washed with 0.1% hydrochloric acid, with brine, and was dried /MgSO$_4$/. The solvent was evaporated and the residue was applied on a column with silica gel /MN 100–200, 8 g/. Elution of the column with a mixture of hexane and ethyl acetate /9:1/ yielded the title compound /200 mg, 72%/; $\gamma_{max}$ 1685 /C=O/, 1625 /C=C/ cm$^{-1}$; $^1$H NMR /CDCl$_3$/ δ /ppm/ 0.8–0.9 /singlet overlapping triplet, 12H, SiCCH$_3$ and CH$_2$CH$_3$/, 1.2–2.6 /m, 14H/, 3.30 and 3.32 /2s, 3H, OCH$_3$/, 3.9 /m, 1H, C$_5$H/, 4.43 /m, 1H, C$_{6a}$H/, 5.9 /m, 1H, C$_2$H/, 6.08 and 6.13 /2d, J=16 Hz, 1H, C$_2$H/, 6.60 and 6.63 /2m, 1H, C$_1$H/

High resolution: mass spectrum for $C_{22}H_{40}O_4Si$ calculated: M$^+$=396,2695. found: M$^+$=396,2697

EXAMPLE VII

Obtaining of 4β-/3'-oxo-1'-octene-1'-yl/-5α-/t-butyldimethylsilyloxy/-2ξ-methoxy-3,3aβ,4,5,6,6aβ-hexahydro-2H-cyclopenta[b]furane [formula 3, X=—CH=CHCO—nC$_5$H$_{11}$, Y=CHOCH$_3$, Z=Si/t-C$_4$H$_9$//CH$_3$/$_2$].

Operations as in example II until the moment of adding boron trifluoride etherate, and then, after 10 minutes, 1,2-epoxyheptane /formula 8, R$^1$=H, R$^2$=n-C$_5$H$_{11}$/ /130 mg, 1.1 mmole/ was added dropwise. Temperature of the reaction mixture was raised to −20° C. during 2 hours and the said temperature was maintained for further 16 hours. After that time a solution of ammonium chloride in tetrahydrofurane was added, the whole was diluted with methylne chloride and the mixture thus obtained was washed with brine, dried /MgSO$_4$/ and the solvent was evaporated under reduced pressure. The obtained product was crude 4β-[1'ξ-/benzensulphonyl/-3'ξ-hydroxy-1'-octyl]-5α-/t-butyldimethylsilyloxy/-2ξ-methoxy-3,3aβ,4,5,6,6aβ-hexahydro-2H-cyclopenta[b]furane [formula 6, Ar=C$_6$H$_5$, B=—CH$_2$—CH/OH/—nC$_5$H$_{11}$, Y=—CHOCH$_3$, Z=Si/t-C$_4$H$_9$//CH$_3$/$_2$] /500 mg/, which was dissolved in methylene chloride /5 ml/ and treated with pyridinium chlorchromate /300 mg/. After 2 hours the mixture was diluted with ether /20 ml/, the solution was decanted from above inorganic salts and the residue was washed with ether. The combined organic solutions were evaporated and the residue was again dissolved in methylene chloride /5 ml/ containing triethylamine /0.5 ml/. After 24 hours the reaction mixture was applied on a column with silica gel /30 g/ and the column was extracted with methylene chloride. The compound thus obtained was identical with the one obtained in example VI.

EXAMPLE VIII

Obtaining of 4β-/2'-methyl-1'-octene-1'-yl/-5α-/t-butyldimethylsilyloxy/-2ξ-methoxy-3,3aβ,4,5,6,6aβ-hexahydro-2H-cyclopenta[b]furane [formula 3, X=—CH=C/CH$_3$/C$_6$H$_{13}$, Y=CHOCH$_3$, Z=Si/-t—C$_4$H$_9$//CH$_3$/].

Operations as in example II until the moment of adding boron trifluoride etherate, and then, after 10 minutes, octanone-2 /128 mg, 1 mmole/ was added dropwise. Temperature of the reaction mixture was raised to +20° C. during about 1 hour and a solution of ammonium chloride in tetrahydrofurane was added. The whole was diluted with chloroform /50 ml/, washed with brine, dried /MgSO$_4$/ and the solvent was evaporated under reduced pressure. The residue /520 mg/ was subject to chromatography on selica gel, with the use of chloroform for elution. The obtained product was 4β-[1'ξ-/benzensulphonyl/-2'ξ-hydroxy-2'ξ-methyl-1'-octyl]-2ξ-methoxy-3,3a,4,5,6,6aβ-hexahydro-2H-cyclopenta[b]furane [formula 6, Ar=C$_6$H$_5$, B=C/OH//CH$_3$/-nC$_6$H$_{13}$, Y=CHOCH$_3$, Z=Si/t-C$_4$H$_9$/CH$_3$/$_2$]/170 mg, 30%/ showing the following properties: infrared spectrum $\gamma_{max}$ 3500 /OH/, 1300 and 1125 /SO$_2$C$_6$H$_5$/, 1250 and 1260 /CH$_3$Si and nC$_4$H$_9$Si/, 1100–1050 /C—O—C, C—O—Si/ cm$^-$; spectrum $^1$H NMR /CDCl$_3$/, δ/ppm/ 8.00–7.31 /m, 5H, aromatic H/, 5.10 /m, 1H, C$_2$H/, 4.41 /m, 1H, C$_{6a}$H/, 4.11 /m, 1H, C$_4$H/, 3.32 and 3.30 /two singlets, 3H, OCH$_3$/, 2.85 /m, 1H, C$_1$,H/, 1.61 and 1.63 /two singlets, 3H, SiCH$_3$/, 0.74 /s, 9H, SiCCH$_3$/.

The above described product was dissolved in methanol /2 ml/ and treated with sodium amalgam /6% Na/ in the atmosphere of argon, at a room temperature, during 14 hours. After that time the solution was decanted from above remainders of amalgam, diluted with hexane /30 ml/, washed with a saturated solution of ammonium chloride and brine, dried /MgSO$_4$/, and the solvent was evaporated under reduced pressure. The residue /84 mg/ was subject to chromatography on silica gel /2 g/, with the use of a mixture of toluene and hexane at the ratio of 4:1 for elution. The title product in the form of oil /72 mg/ was obtained, infrared spectrum $\gamma_{max}$ 1450 /C=C/, 1260, 1250 /CH$_3$Si, nC$_4$H$_9$Si/, 1170, 1150, 1060 /C—O, Si—O/ cm$^{-}$; spectrum $^1$H NMR /CDCl$_3$/ $\delta$/ppm/ 0.83 /s, 9H, SiCCH$_3$/, 1.68 /m, 3H, C=C—CH$_3$/, 3.33 and 3.29 /2s, 3H, OCH$_3$/, 3.69 /m, 1H, C$_5$H/, 4.41 /m, 1H, C$_{6a}$H/, 4.80 /m, 1H, C=CH/, 5.07 /m, 1H, C$_2$H/.

Mass spectrum of high resolution for C$_{23}$H$_{44}$O$_3$Si calculated: M$^+$=396,3060 found: M$^+$=396,3060.

EXAMPLE IX

Obtaining of 4$\beta$-[3'-oxo-4'-/m-chlorphenoxy/-1'-buten-1'-yl]-5$\alpha$-/t-butyldimethylsilyloxy/-2$\xi$-methoxy-3,3a$\beta$,4,5,6,6a$\beta$-hexahydro-2H-cyclopenta[b]furane [formula 3, X=—CH=CHCOCH$_2$—O—/m-ClC$_6$H$_4$/, Y=CHOCH$_3$, Z=Si/t-C$_4$H$_9$/CH$_3$/2].

To a solution of 4$\beta$-/benzensulphonylmethyl/-5$\alpha$-/t-butyldimethylsilyloxy/-2$\xi$-methoxy-3,3a$\beta$,4,5,6,6a$\beta$-hexahydro-2H-cyclopenta[b]furane [formula 4, Ar=—C$_6$H$_5$, Y=CHOCH$_3$, Z=Si/t-C$_4$H$_9$/CH$_3$/2]/427 mg, 1 mmole/ in tetrahydrofurane /5 ml/, mixed in the atmosphere of argon at the temperature of —72° C., n-butyllithium /1.4 M in hexane, 0.76, 1.1 mmole/ was added. The mixture was maintained at the temperature of —72° C. for 30 minutes, and then boron trifluoride etherate /0,125 ml, 1 mmole/ was added and, subsequently, 1,2-epoxy-3-/m-chlorphenoxy/-propane [formula 8, R$^1$=H, R$^2$=—CH$_2$—O—/mCl—C$_6$H$_4$/] /185 mg, 1 mmole/. The reaction mixture was maintained for 2 hours at the temperature of —72° C., and thereafter the temperature was raised to 0° C. during about 1 hour and a saturated solution of ammonium chloride /0.5 ml/ was added. The mixture was extracted with methylene chloride /2×5 ml/, the combined extracts were washed with brine and dried /MgSO$_4$/. The solvent was evaporated, and the residue (660 mg/ was applied on a column with silica gel /MN 100-200, 12 g/. Elution of the column with a mixture of toluen and ethyl acetate of 10-: yielded 4$\beta$-[1'$\xi$-/benzensulphonyl/-3'$\xi$-hydroxy-4'-/m-chlorphenoxy/-1'-butyl]-5$\alpha$-/t-butyldimethylsilyloxy/-2$\xi$-methoxy-3,3a$\beta$,4,5,6,6a$\beta$-hexahydro-2H-cyclopenta[b]furane [formula 6, Ar=C$_6$H$_5$, B=CH$_2$CH/OH/CH$_2$O/m-ClC$_6$H$_4$/, Y=CHOCH$_3$, Z=Si/t-C$_4$H$_9$//CH$_3$/2]/580 mg, 95%/; $\gamma_{max}$ /film/ 3600-3200 /OH/, 1600, 1585, 1480, 1450 /aromat/, 1315 /SO$_2$C$_6$H$_5$/ cm$^{-1}$; $^1$H NMR $\delta$/ppm/ 0.8-0.92 /m, 9H, SiCCH$_3$/, 1.50-2.7 /m, 9H/, 3.30 /s, 3H, OCH$_3$/, 3.6-4.1 /m, 4H, C$_5$H, C$_3$,H, C$_4$,H$_2$/, 4.45 /m, 1H, C$_{6a}$H/, 5.06 /m, 1H, C$_2$,H/, 6.70-7.12 /m, 4H, aromat.H/, 7.4-7.6 /m, 3H, aromat. H/, 7.96 /m, 2H, aromat. H/.

Elementary analysis Calculated for C$_{30}$H$_{43}$ClO$_7$SSi %C—58.95; %H—7.09. Found: /6 15.26/ %C—59.04; %H—7.40

The above described compound /550 mg, 0.9 mmole/ was dissolved in methylene chloride /1.5 ml/ and was added dropwise at the temperature of —50° C., in the atmosphere of argon, at intense stirring, to an oxidizing mixture prepared, as follows: to a mixture of oxalyl chloride /0.085 ml, 0.97 mmole/ and methylene chloride /2 ml/ cooled to —50° C. and mixed in the atmosphere of argon a mixture of dimethylsulphoxide /0.14 ml, 1.97 mmole/ and methylene chloride /0.5 ml/ was added. The reaction mixture was maintained at the temperature of —50° C. for 30 minutes, triethylamine /0.6 ml, 4.3 mmole/ was added, stirring at the temperature of —50° C. was being carried on for 5 minutes, and thereafter the cooling bath was removed. When the reaction mixture reached the room temperature /about 1 hour/, water /5 ml/ was added and the whole was extracted with methylene chloride /3×5 ml/. The combined extracts were washed with brine and dried /MgSO$_4$/. The solvent was evaporated, and the residue /500 mg/ was applied on a column with silica gel /MN 100–200, 10 g/. Elution of the column with a mixture of toluene and ethyl acetate 9:1 yielded:

1/ 4$\beta$-[3'-oxo-4'-/m-chlorphenoxy/-1'-butene-1'-yl]-5$\alpha$-/t-butyldimethylsilyloxy/-2$\xi$-methoxy-3,3a$\beta$,4,5,6,6a$\beta$-hexahydro-2H-cyclopenta[b]furane /280 mg/; $\gamma_{max}$ /film/ 1695 /C=O/, 1630./C=C/, 1595, 1580, 1485, 1445 /aromat/, 1260, 840 cm$^{-1}$; $^1$H NMR /CDCl$_3$/ $\delta$/ppm/ 0.022 and 0.030 /2s, 6H, SiCH$_3$/, 0.87 /s, 9H, SiCCH$_3$/, 1.65-2.19 /m, 3H/, 2.28-2.61 /m, 2H/, 2.73-3.01 /m, 1H/, 3.34 and 3.38 /2s, 3H, OCH$_3$/, 3.69-4.10 /m, 1H, C$_5$H/, 4.38-4.60 /m, 1H, C$_{6a}$H/, 4.71 /s, 2H, C$_4$,H/, 5.06-5.15 /m, 1H, C$_2$H/, 6.45 and 6.49 /2d, J=15.6 Hz, 1H, C$_2$,H/, 6.73-7.23 /m, 5H, C$_1$,H, and aromat. H/.

Elementary analysis Calculated for C$_{24}$H$_{35}$ClO$_5$Si: %C—61.72; %H—7.55. Found: /467.07/ %C—61.44; %H—7.63.

2/4$\beta$-[1'$\xi$-/benzensulphonyl/-3'-oxo-4'-/m-chlorphenyl/-1'-butyl]-5$\alpha$-/t-butyldimethylsilyloxy/-2$\xi$-methoxy-3,3a$\beta$,4,5,6,6a$\beta$-hexahydro-2H-cyclopenta[b]furane [formula 6, Ar=C$_6$H$_5$, B=CH$_2$COCH$_2$O/mClC$_6$H$_4$/, Y=CHOCH$_3$, Z=Si/t-C$_4$H$_9$//CH$_3$/2] /155 mg/, $\gamma_{max}$ /film/ 1745 /C=O/ cm$^{-1}$.

EXAMPLE X

Obtaining of 4$\beta$-/3',4'-isopropylidenedioxy-1'-buten-1'-yl/-5$\alpha$-/t-butyldimethylsilyloxy/-2$\xi$-methoxy-3,3a$\beta$,4,5,6,6a$\beta$-hexahydro-2H-cyclopenta[b]furane [formula 3, X=group of the formula 15, Y=CHOCH$_3$, Z=Si/t-C$_4$H$_9$//CH$_3$/2].

Operations as in example II until the moment of adding boron trifluoride etherate, and then, after 10 minutes, a solution of /S/ O,O'-isopropylidenglyceric aldehyde /162 mg, 1.25 mmole/ in benzene /0.3 ml/ was added dropwise. The reaction mixture was maintained at the temperature of —60° C. for 2 hours, and then the temperature was raised to 0° C. during 1 hour. After that time a saturated aqueous solution of ammonium chloride /0.5 ml/ was added, the mixture was extracted with methylene chloride /3×10 ml/, the combined extracts were washed with brine and dried /MgSO$_4$/. The solvent was evaporated and the residue /620 mg/ was subject to chromatography in a column with silica gel /60 g/, with the use of a mixture of hexane and ethyl acetate at the ratio of 3:1 for elution. The obtained product was 4$\beta$-[3',4'-isopropylidendioxy-2'$\xi$-hydroxy-1'$\xi$-benzensulphonyl/-but-1'-yl]-5$\alpha$-/t-butyldimethylsilyloxy/-2$\xi$-methoxy-3,3a$\beta$,4,5,6,6a$\beta$-hexahydro-2H- cyclopenta[b]furane [formula 6, Ar=$C_6H_5$ B=group of the formula 16, Y=$CHOCH_3$, Z=Si/t-$C_4H_9$//$CH_3$/$_2$] /484 mg/ in the form of colourless oil; $\gamma_{max}$ 3400 /OH/ $cm^{-1}$.

To a solution of the above compound /426 mg, 1 mmole/ in tetrahydrofurane /2.5 ml/, mixed in the atmosphere of argon, at the temperature of −78° C., n-butyllithium /1.4 M in hexane, 1.1 mmole/ was added. Stirring was being carried on for 30 minutes, and thereafter benzoyl chloride /0.126 ml, 1.09 mmole/ was added. The mixture was heated to a room temperature during 3 hours, 3-/dimethylamino/-1-propylamine /0.1 ml/ was added, then water was added, and the mixture thus obtained was extracted with methylene chloride /3×10 ml/. The combined extracts were dried /$MgSO_4$/, the solvent was evaporated, and the residue was applied on a column with silica gel. Washing of the column with a mixture of hexane and ethyl acetate of 3:1 yielded a benzoyl derivative in the form of colourless oil /500 mg/. The said compound was dissolved in tetrahydrofurane /6 ml/, in the atmosphere of argon, 6% sodium amalgam /1 g/ was added and, after cooling the mixture to the temperature of −20° C., methanol /2 ml/. The whole was being stirred for 3 hours at the temperature of −20° C. After that time a saturated aqueous solution of ammonium chloride /0.5 ml/ was added, then water, and the mixture thus obtained was extracted with methylene chloride /3×10 ml/. The combined extracts were dried /$MgSO_4$/, the solvent was evaporated and the residue was subject to chromatography on a column with silica gel, with the use of a mixture of hexane and ethyl acetate of 6:1 for elution. The obtained title product /180 mg, 52%/ was identical with the reference.

EXAMPLE XI

Obtaining of 4β-[3'-/t-butyldimethylsilyloxy/-1'-octene-1'-yl]-5α-/t-butyldimethylsilyloxy/-2ξ-methoxy-3,3aβ,4,5,6,6aβ-hexahydro-2H-cyclopenta[b]furane [formula 3, X=—CH=CH—CH [OSi/-t—$C_4H_9$//$CH_3$/$_2$]—$nC_5H_{11}$, Y=$CHOCH_3$, Z=Si/-t—$C_4H_9$//$CH_3$/$_2$].

By the method described in example II 4β-[1'ξ-/benzensulphonyl/-2'ξ-hydroxy-3'ξ-/t-butyldimethylsilyloxy/-1'-octyl]-5α-/t-butyldimethylsilyloxy/-2ξ-methoxy-3,3aβ, 4,5,6,6aβ-hexahydro-2H-cyclopenta[b]furane was obtained [formula 6, Ar=$C_6H_5$, B=CH/OHCH OSi/t—$C_4H_9$//$CH_3$/$_2$ $C_5H_{11}$, Y=-$CHOCH_3$, Z=Si/t—$C_4H_9$//$CH_3$/$_2$]. To a solution of the above compound /671 mg, 1 mmole/ in pyridine /15 ml/, mixed in the atmosphere of argon, at the temperature of −10°° C., methansulphonic chloride /0.3 ml, 4 mmoles/ was added and the mixture thus obtained was maintained for 16 hours at the temperature of +5° C. Next, the reaction mixture was concentrated to about 1/5 of volume, diluted with toluene /10 ml/ and washed with cooled 3% hydrochloric acid, with brine and with a saturated solution of $NaHCO_3$. The solution was dried with $MgSO_4$ and the solvent was evaporated. The residue /700 mg/ was subject to chromatography on silica gel /10 g/, being eluted with a mixture of toluene and ethyl acetate 98:2. Methansulphonate /600 mg, 80%/ was obtained. The said compound was dissolved in absolute methanol /7 ml/ and to a solution, mixed in the atmosphere of argon, powder $Na_2HPO_4$ /660 mg/ was added. The mixture was cooled to the temperature of −40° C. and 6% sodium amalgam /2.2 g/ was added in portions thereto during about 30 minutes. The cooling bath was removed and when the reaction mixture reached a room temperature—about 1 hour—a saturated solution of ammonium chloride /3 ml/ was added thereto, and then water. The mixture was extracted with toluene /3×10 ml/, the combined extracts were dried with $MgSO_4$ and the solvent was evaporated under reduced pressure. The residue was subject to chromatography on silica gel /10 g/, elution being carried out with the use of a mixture of toluene and ethyl acetate of the ratio of 98:2. The title compound obtained /344 mg, 85%/ was identical with the standard.

EXAMPLE XII

Obtaining of 4β-/2'-phenylethen-1'yl/-5α-/t-butyl-dimethylsilyloxy/-2ξ-methoxy-3,3aβ,4,5,6,6aβ-hexahydro-2H-cyclopenta[b]furane [formula 3, X=—CH=CH—$C_6H_5$, Y=$CHOCH_3$, Z=Si/t—$C_4H_9$//$CH_3$/$_2$].

By the method described in example IV 4β-[1'ξ-/benzensulphonyl/-2'ξ-hydroxy-2'-phenyl-1'-ethyl]-5α-/t-butyldimethylsilyloxy/-2ξ-methoxy-3,3aβ,4,5,6,6aβ-hexahydro-2H-cyclopenta[b]furane [formula 6, Ar=$C_6H_5$, B=CH/OH/$C_6H_5$, Y=$CHOCH_3$, Z=Si/-t—$C_4H_9$//$CH_3$/$_2$]/500 mg/ was obtained.

To a solution of the above compound /475 mg, 0.89 mmole/ and 1.10 phenanthrolein /1 mg/ in tetrahydrofurane /3 ml/, mixed at the temperature of −78° C., in the atmosphere of argon, n-butyllithium /1M in hexane/ was being added until dark colour appeared. After 30 minutes benzoyl chloride /0.13 ml, 1.112 mmole/ was added dropwise, the cooling bath was removed and the reaction mixture was let to reach the room temperature /during 3 hours/. Next, 3-/dimethylamino/-1-propylamine /0.1 ml/ was added, the mixture was diluted with water and extracted with methylene chloride /3×10 ml/. The combined extracts were dried /$MgSO_4$/, the solvent was evaporated, and the residue was applied on a column with silica gel /400 mesh/. Washing of the column with a mixture of hexane and ethyl acetate /5:1/ and evaporation of the solvent yielded a benzoyl derivative in the form of colourless oil /550 mg/. The said product was dissolved in tetrahydrofurane /6 ml/, in the atmosphere of argon, sodium amalgam 6% /1 g/ was added, the mixture was cooled to −20° C., and thereafter methanol /2 ml/ was added. Stirring at the temperature of −20° C. was baing carried on for 3 hours, and thereafter a saturated aqueous solution of ammonium chloride /0.5 ml/ was added. The reaction mixture was diluted with water and extracted with methylene chloride /3×10 ml/. The combined extracts were dried /$MgSO_4$/, the solvent was evaporated, and the residue was subject to chromatography on a column with silica gel, a mixture of hexane and ethyl acetate /15:1/ being used for elution. The tile product was obtained /178 mg/ in the form of colourless oil, identical with the authentic reference.

EXAMPLE XIII

Obtaining of Prostaglandin $F_{2\alpha}$

4β-[3'ξ-/t-butyldimethylsilyloxy/-1'-octene-1'-yl]-5α-/t-butyldimethylsilyloxy/-2ξ-methoxy-3,3aβ,4,5,6-,6aβ-hexahydro-2H-cyclopenta[b]furane /obtained as specified in example II/ /197 mg, 0.4 mmole/ was dissolved in a mixture of acetonitrile and water /2:1, 2 ml/, hydrochloric acid was added and the mixture was left alone at a room temperature for 16 hours. Next, the mixture was concentrated under reduced pressure, toluene was added thereto and the organic layer was separated. The aqueous layer was extracted with toluene /3×5 ml/. The combined organic extracts were washed with brine, dried /MgSO4/ and the solvent was evaporated undr reduced pressure. The residue /150 mg/ was applied on a column with silica gel /12 g/ and the column was washed with a toluene-chloroform-methanol mixture /10:5:1/, what yielded 4β-/3'ξ-hydroxy-1'-octene-1'-yl/-2ξ,5α-dihydroxy-3,3aβ,4,5,6,6aβ-hexahydro-2H-cyclopenta[b]furane [formula 3, X=—CH=CH/OH/—nC5H11, Y=CHOH, Z=H/]/97 mg, 90%/; $\gamma'_{max}$ 3350 /OH/, 1650 /C=C/, 1100-1000 /C—O/ cm$^{-1}$; $^1$H NMR /CDCl3/ δ/ppm/ 3.95 /m, 2H, CHO$\underline{H}$/, 4.42 /m, 1H, C$_{6a}\underline{H}$/, 5.28 /m, 1H, C$_2\underline{H}$/, 5.55 /m, 2H, C=C$\underline{H}$/.

The above described compound /97 mg, 0.36 mmole/ was dissolved in dimethylsulphoxide /1 ml/ and the solution thus obtained was added to a solution of ylid prepared, as follows: a solution of sodium salt of dimethylsulphoxide /dimsyl sodium/ in dimethylsulphoxide /1.7M, 1.2 ml, 2 mmoles/ was added dropwise to a solution of triphenyl/4-carboxybutyl/phosphonate bromide /433 mg, 1 mmole/ in dimethylsulphoxide /1 ml/. The whole was being stirred for 1 hour at a room temperature and for 1 hour at the temperature of 50° C., and thereafter was diluted with water /5 ml/ and extracted with ethyl acetate /2×20 ml/. The aqueous layer was acidified with diluted hydrochloric acid and extracted with ethyl acetate /2×20 ml/. The combined organic extracts were washed with brine, dried /MgSO4/ and the solvent was evaporated under reduced pressure. The residue /500 mg/ was applied on a column with silica gel /0.06-0.08 mm, Merck, 25 g/ and the column was eluted with a toluene-chloroform-methanol mixture of the ratio of 17:5:2, what yielded: rac-15-epi-PGF$_{2\alpha}$ /30 mg/ and rac PGF$_{2\alpha}$ /28 mg/ identical with the reference sample.

What is claimed is:

1. A method of obtaining derivatives of 4beta-1'-alken-1'-yl-2,5alpha-dihydroxy,3,3a beta-hexahydro-2H-cyclopenta[b]furan of the formula 3,

FORMULA 3 in which Z denotes a hydrogen atom or a protective group, Y denotes a group of the formula =CHOZ$^1$, in which Z$^1$ has the meaning stated for Z, whereby protective groups Z and Z$^1$ may be the same or different, and X denotes a straight or branched alkenyl chain corresponding to a side chain ω of prostaglandins or their analogs, comprising reacting a sulphonyl derivative of the formula 4,

FORMULA 4 in which Y and Z have the above stated meaning and Ar denotes an aryl group, with a strongly basic organometallic compound and a metal salt selected from the group consisting of zinc, titanium, magnesium and boron halides and then with an electrophilic agent of the formula 5,

FORMULA 5 in which one of R$^1$ and R$^2$ denotes a hydrogen atom and the other one denotes a straight or branched alkyl group or the other one of R$^1$ and R$^2$ denotes an aryl group, or in which R$^1$ and R$^2$ denote the same or different alkyl, and thereafter the obtained intermediate compound of the formula 6,

FORMULA 6 in which Y and Z have the above stated meaning, and B denotes a group of the formula 7,

FORMULA 7 in which Ar, R$^1$ and R$^2$ have the above stated meaning, is reduced.

2. A method according to claim 1, wherein protective groups are removed at the end of the process.

3. A method according to claim 1, wherein said intermediate compound of the formula 6 is converted to an ester, before reduction by means of acylating or sulphonylating agents.

4. A method according to claim 2, wherein said intermediate compound of the formula 6 is converted to an ester, before reduction, by means of acylating or sulphonylating agents.

5. A method as in claim 1, wherein the ω chain of said formula 3 is substituted with one of the group consisting of hydroxy, protected hydroxy, oxo protected oxo, aryl, aryloxy, substituted aryloxy, and substituted aryl.

6. A method as in claim 1, wherein said Ar group of formula 4 may be a substituted aryl group.

7. A method as in claim 1, wherein said formula 5 is substituted with one of the group consisting of hydroxy, protected hydroxy, oxo, protected oxo, aryloxy, substituted aryloxy, aryl aand substituted aryl.

8. A method as in claim 1, wherein when R$^1$ or R$^2$ of formula 5 denotes an aryl group, said aryl group is a substituted aryl group.

9. A method as in claim 7, wherein, when one of R$^1$ or R$^2$ of formula 5 is alkyl, said alkyl is substituted.

* * * * *